United States Patent [19]

Gardella et al.

[11] Patent Number: 4,544,356
[45] Date of Patent: Oct. 1, 1985

[54] RECIPROCATING DENTAL PROPHYLACTIC ANGULAR DEVICE

[75] Inventors: John M. Gardella, Matawan, N.J.; Casimir Ciepierski, Staten Island, N.Y.; Michael Alfano, Franklin Lakes; Tiang-Shing Chang, Westfield, both of N.J.

[73] Assignee: Block Drug Company Inc., Jersey City, N.J.

[21] Appl. No.: 671,739

[22] Filed: Nov. 15, 1984

[51] Int. Cl.$^4$ .............................................. A61C 1/07
[52] U.S. Cl. .................................... 433/122; 433/125
[58] Field of Search ............... 433/118, 122, 123, 124, 433/125; 74/53

[56] References Cited

U.S. PATENT DOCUMENTS

| | | | |
|---|---|---|---|
| 733,398 | 7/1903 | Joseph | 433/122 |
| 1,711,846 | 5/1929 | Heilborn | 433/122 |
| 2,135,933 | 11/1938 | Blair | 433/122 |
| 3,555,685 | 1/1971 | Loge | 433/122 |
| 4,371,341 | 2/1983 | Nakanishi | 433/118 |

*Primary Examiner*—John J. Wilson
*Attorney, Agent, or Firm*—Ostrolenk, Faber, Gerb & Soffen

[57] ABSTRACT

A dental prophylactic device has a handle section containing a drive member and a driven section at a substantial angle to the handle section containing a driven member also at an angle to the driving member. The handle section includes a longitudinally oscillatable cam follower supported parallel to the handle axis. When the cam follower is translated around the axis by the rotation of the drive shaft, it is caused to oscillate by one end contacting the stationary cam follower track. The other end engages a slot parallel to the axis of a cam at an angle to the cam follower thereby causing the cam to oscillate back and forth over an arc of at least 50° to approximately 150°, maintaining the connection between the cam follower and the cam by the use of the slot which permits the cam follower, in effect, to move up and down with respect to the cam as it oscillates. The cam oscillates a cup which may contain prophylactic material and the reversing action limits the ability of the material to be thrown out of the cup and obviates unintended movement of the cup over the surface of a tooth which occurs in the case of rotation in a single direction. A special sealing ring and its compartment, remotely located from the head of the spindle, provides an excellent seal.

7 Claims, 6 Drawing Figures

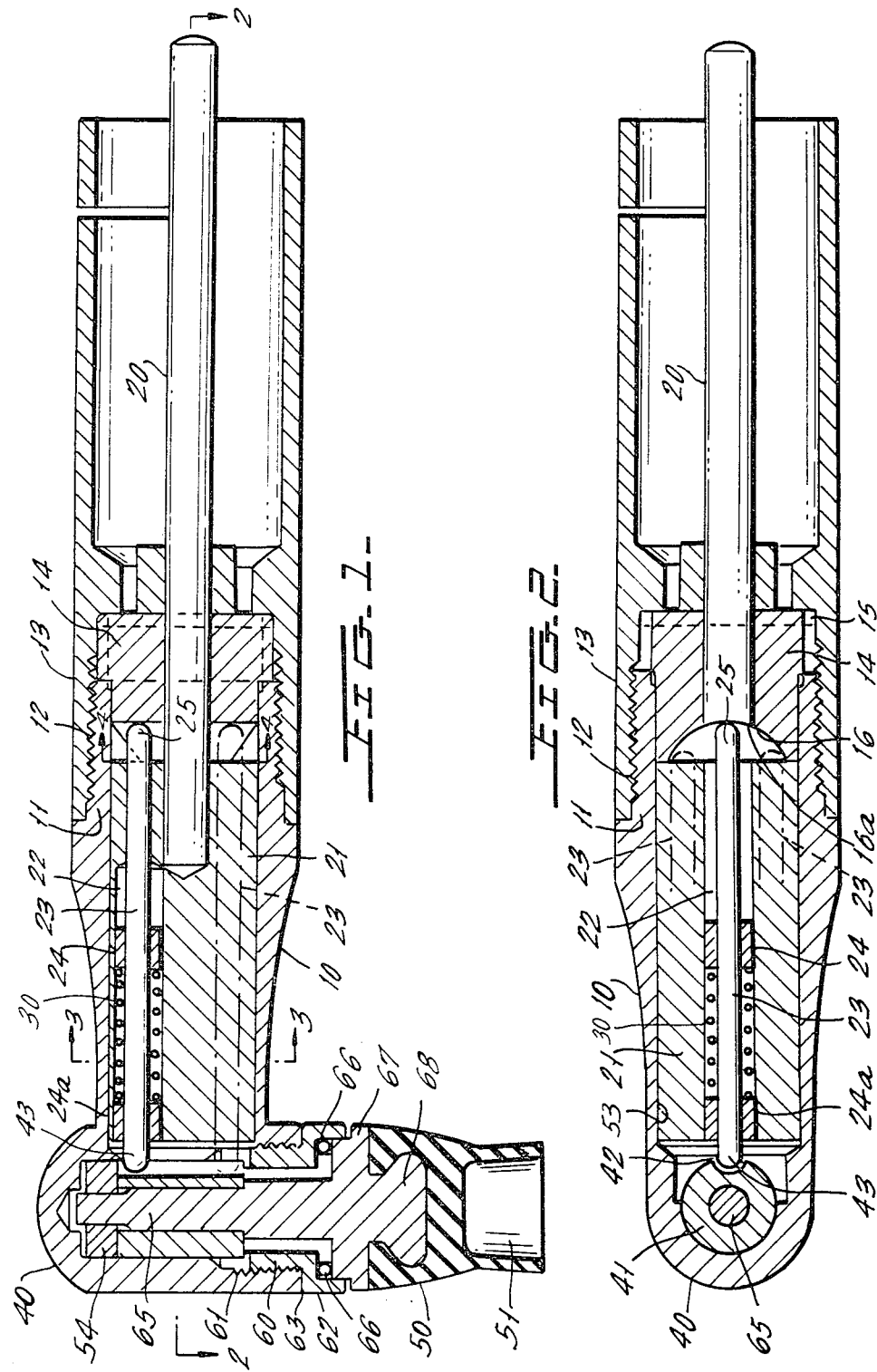

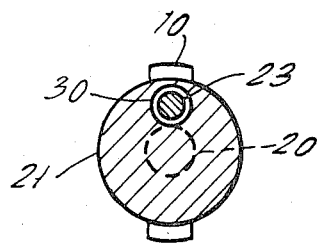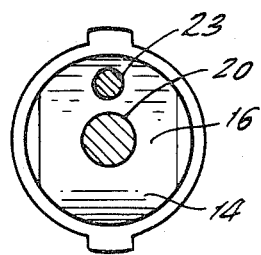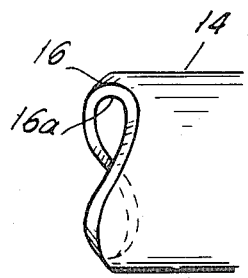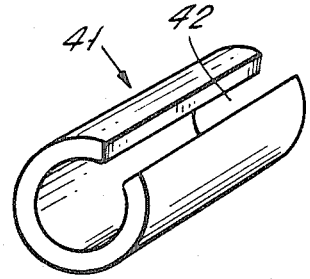

RECIPROCATING DENTAL PROPHYLACTIC ANGULAR DEVICE

BACKGROUND OF THE INVENTION

The present invention relates to an angular drive for a dental prophylactic device or cup which may contain prophylactic material for massage into the tooth, and which is adapted to polish or otherwise treat the surface of a tooth.

Essentially, the present structure is a handheld tool which may be operated in any suitable manner as from the main drive of the dental handpiece, either belt, air or electrically driven, or in any other manner and which will provide an appropriate handle structure so that the device may readily be grasped by the user. In addition, it is necessary that the handle be structured in such a manner so as to facilitate the application of the prophylactic material to the operating surface of the tooth, i.e., at an angle approximately 90° to the handle itself.

In the present invention, the handle carries the internal drive means for the particular operating device and the interconnecting elements between the operating elements and the application device. Heretofore, in applying a paste by rotary means to a tooth, the rotational speeds are limited in traditional prophylactic angled devices because centrifugal forces cause the prophylactic paste to fly off the rotating prophylactic cup when speeds are increased beyond approximately 2,000 to 2,500 rpm. This condition requires either the utilization of relatively low speeds or of viscous pastes which are not necessarily optimum for prophylaxis.

An important feature and object of the present invention is the replacement of the rotating, polishing and prophylactic carrying cup with a cup which oscillates through an arc of at least 50° to approximately 150°. In the operation of the device, according to the present invention, the stopping and reverse rotation will stop the paste from moving off the cup. As a result, oscillation cycles may be increased to as much as 12,000 rpm without the presently known problem of the paste flying off the cup. This increased oscillation cycling speed should result in improved tooth cleaning efficiencies and also make possible the utilization of various new types of prophylactic pastes.

Also, in the operation of prophylactic devices of the type herein referred to, a constant rotation in a single direction causes the device to move off the particular location on the tooth in a direction dictated by rotational forces so that full control is maintained only with application of a constant counterforce on the handle.

An object of the present invention, therefore, is, by use of a reciprocating device, to obviate the result which occurs from constant rotation in a single direction and makes the instrument drift from a spot on which it is being used and is intended to be used.

One of the major problems in the operation of prophylactic devices using rotational movement is generated by the use of the toothed drive gears in the angular drive from the structure in the handle to the operating structure. These right angle gears, when operated at speeds of 1,500 to 2,500 rpm, tend to act like a pump pulling the debris, saliva and foreign matter into the angle head and so causing malfunction and premature wear. This necessitated the need to add seals to the construction of traditional angular driving devices to reduce this objectionable condition.

A further object of the present invention, therefore, is the utilization of a reciprocating cam follower translated into an oscillating motion at the cup to obtain smoother running and a longer life, thus obviating the need for gears and their inherent problems also enabling the provision of a seal which will be able to retain lubricants inside the angularly disposed head.

In addition to the advantages which accrue from the oscillating motion of the cleaning cup, a longer arc of oscillation is made possible, that is an arc of oscillation of the order of 120°, providing for more positive action. This is obtained through the utilization of an oscillating longitudinal cam follower which oscillates axially of the drive shaft and is translated into the oscillating motion of the prophylactic cup by a slot in the surface of the oscillating cam carrying the cup which is parllel to its axis and is engaged by the longitudinal member. The longitudinal member, as it is translated around the axis of the drive, is oscillated by its contact with the stationary cam follower track which is concave surfaced and which causes the longitudinal member to oscillate when it is translated around the axial center of the drive.

Another and important object of the present invention, therefore, is the provision of a longitudinal oscillating cam follower interconnected with a slot parallel to the axis of the angled applying cup wherein the longitudinal oscillation of the cam follower is simply obtained by having the cam follower arranged parallel to the axis of the drive member and translating the same around the axis of the drive member while the cam follower, optionally, is spring biased against a stationary cam follower track in the drive member which causes the cam follower to oscillate.

It should be borne in mind that this kind of drive may well be utilized in other dental operating devices such as endodontic reamers, broaches and other canal opening devices.

The present invention, therefore, also has an object the provision of a structure which permits the utilization and impingement of greater loads or torque on the prophylactic cup during prophylaxis because of the positive action of the mechanism, thereby further improving cleaning and other operating efficiencies.

BRIEF DESCRIPTION OF THE DRAWINGS

The foregoing and many other objects of the present invention will become apparent from the following description and drawings in which:

FIG. 1 is a longitudinal cross-sectional view of the operating elements of the device of the present invention taken through the drive mechanism and the oscillating cup;

FIG. 2 is a cross-sectional view taken from line 2—2 of FIG. 1 looking in the direction of the arrows;

FIG. 3 is a cross-sectional view taken on line 3—3 of FIG. 1 looking in the direction of the arrows;

FIG. 4 is a view partly in cross-section taken on line 4—4 of FIG. 1 looking in the direction of the arrows;

FIG. 5 is a view in perspective showing the driven support for the oscillating cup and the slot in the outer surface thereof which is engaged by the operating rod; and FIG. 6 is a schematic view in perspective of the stationary cam of FIGS. 1 and 2.

DETAILED DESCRIPTION OF THE INVENTION

Referring to the figures, the novel prophylactic device of the present invention comprises a tapered cylindrical housing 10 connected by the neck 11 and the screw thread 12 thereon to the handle housing 13. The neck 11 of the housing 10 supports a cylindrical block 14 therein which is stationarily connected to the housing and may be essentially integrated therewith by the utilization of the key members 15 engaging appropriate slots at the end of the neck 11 of the housing.

The forward end, that is the end directed toward the driven end of the device, of the block 14 is provided with the cam 16. The said cam is arranged so that it will provide oscillation for the driving rod as hereinafter described.

The housing section 10 and 13 thus form a housing for the device which may be held in the hand. It is preferred that, in operation, the operator grasp the surface of the housing section 13 which may be appropriately frictionally treated or scored to simplify the grip, but the operator may also extend the fingers toward the housing section 10.

The housing section 13 contains the drive shaft 20 which is driven in any suitable manner, usually by a belt, air or electrically driven handpiece connected to the dental unit. The shaft 20 is connected to and drives the cylindrical block 21 carried internally of the housing section 10. The cylindrical block 21 is provided with a longitudinal bore 22 parallel to the axis thereof. This bore 22 is displaced from the axis of rotation as indicated by the additional dotted lead line to the additional reference numeral 22. The said longitudinal bore 22 contains the operating rod 23 which is mounted for axial oscillation. The displacement of rod 23 from the axis of rotation is also indicated by the additional dotted lead line to the additional reference number 23. Rod 23 is guided in bore 22 by the collar 24 secured to rod 23 and by the bushing 24a in bore 22. Rod 23 is provided with the cam follower head 25 which bears against the inner surface of the cam 16. As the shaft 20 rotates, rotating also the block 21 with its bore 22 and the rod 23 which is carried thereby the cam follower head 25 bears against the cam surface 16(a) and is caused to oscillate between the positions shown in the solid and dotted lines of FIG. 1. As seen particularly in FIG. 6, the cam 16 has a cam surface 16a which varies continuously in a manner to cause the rod 23 and its cam follower head 25 to oscillate as the block 21 rotates.

The operating rod 23 drives the cam follower head 25 against the cam surface 16(a) preferably by means of the compression spring 30 which bears on the bushing 24a at the left hand end of the bore 22 and on collar 24 on rod 23 driving the cam follower head 25 of the oscillating rod 23 against the cam surface 16(a) and ensuring thereby that the position of the operating rod 23 is at all times controlled by its relationship to the cam 16.

The front end of the housing 10 is connected to an angular housing 40 which preferably is at right angles to the housing 10. It is desirable that it be at right angles so that the operating rod 23 always has a fixed relationship with the operating mechansims within the housing 40. The upper end of housing 40 may be integral with the end of housing 10 to provide a smooth curved transition and to obviate as far as possible any seams or cracks in which deleterious matter may collect. The housing 40 contains the oscillating cam 41 which is a cylinder having a slot 42 therein parallel to the axis of the cylinder. It will be noted that the cam cylinder 41 extends at right angles to the operating rod 23. The operating rod 23 is provided at its end which extends into the housing 40 with a slot engaging extension 43 which is captured as shown more clearly in FIG. 2 in the slot 42.

The slot engaging section of rod 23 may be the end 43 or may have any desired shape consistent with engagement with slot 42 without passing entirely through slot 42. As the operating rod 23 is thereby moved back and fourth, the slot engaging extension 43 is also caused to be moved back and forth therewith, thereby causing the oscillating cam cylinder 41 to oscillate preferably over an arc of 120° as indicated in FIG. 2. Since the section 21 of the drive member which contains the operating rod containing bore 22 is rotating around an axis which then intersects the axis of the oscillating cam cylinder 41, the interconnection must be a slot so that the operating extenion 43 of the operating rod 23 may move up and down in the slot 42 of the cylinder 41 while performing the operation of moving the cylinder 41 back and forth. The operating end of the cylinder 41 is connected in any suitable manner to the cup base 50 which carries the cup 51 which may be of any suitable material, preferably of material which may be readily placed in contact with the tooth without damaging the tooth. The cup 51 will thus be of relatively softer material which has sufficient flexing ability to provide an appropriate cleaning and recess 52 for carrying prophylactic material. The forward or operating end of the housing 11 has a stationary bearing 53 for th rotating block 21 which carries the rod 23. The front housing 40 of the oscillating cylinder 41 has a bearing 54 for said cylinder. By this means, therefore, a simplified drive is provided for the cup 51 in the hollow section 52 of which prophylactic material may be placed.

The additional housing 40 may be completed in any suitable manner. The head cup 60 may be screw threaded into the threaded section 61 of housing 40 with the flange 62 of head cup 60 bearing against the lower edge 63 of housing 40. The spindle 65 may be held by and positioned by cylinder 41. The O-ring 66 between radial extension 67 of spindle 65 and flange 62 protects the interior of the housing 1014 40 from entry of extraneous material. The lower end 68 of spindle 65 may be shaped to receive and removably hold a prophylactic cup or other dental device.

The utilization of the oscillating rod, cam follower and rod extension into the slot of the oscillating cam cylinder obviates the need for drive gears which may act as suction devices to pull in deleterious material thereby shortening the life of the device and decreasing its sanitary properties.

Better control is provided for the user of the device and higher rates of reciprocating speed may be used in order to enhance the polishing effect.

In the foregoing, the present invention has been described in connection with preferred embodiments thereof. Since many variations and modifications of the present invention will now be obvious to those skilled in the art, it is preferred that the scope of the invention be determined, not by the specific disclosures herein contained, but only by the appended claims.

What is claimed is:

1. A dental device comprising:
   a drive member and a driven member;
   a housing for the drive member and a housing for the driven member;

the driven member comprising an oscillatable cylinder carrying a dental treatment member at the end thereof and at a right angle to the housing for the drive member;

a rotatable member in the drive housing having a longitudinal bore parallel to the axis of rotation and an operating rod in said bore; said operating rod being translatable about the axis of rotation of said rotatable member;

a stationary cam within said housing, said operating rod having a cam follower head at one end operating against said cam and an extension therefrom interengaging a slot in said oscillatable cylinder;

said operating rod being oscillated by said cam on translational rotation of said operating rod, said oscillation of said operating rod causing the cylinder to receiprocate around its axis and the interengagement of the operation rod with the slot permitting the operating rod end to translate around said axis of rotation while engaging said cylinder.

2. The dental device of claim 1, wherein the interengagement of said cam and cam follower head comprises a spring biasing said operating rod and cam follower head against said cam thereby causing the cam rod to oscillate as the operating member is rotated and while the interconnection between the operating rod and the cylinder is maintained.

3. A dental device having a housing for operating elements and an additional housing connected to the handle distally of the operating elements and at an angle to the handle; the handle including an internally rotating member rotating on an axis parallel to the axis of the handle and having a longitudinal bore parallel to the axis of said rotating member, but spaced from said axis of rotation; an operating rod contained within said bore and a stationary cam in said handle, a cam follower head at the end of said operating rod engaging said handle and means causing said cam follower head on said operating rod to follow said cam; a cylinder located in said additional housing, said cylinder having its axis at a substantial angle to the axis of the operating housing, a slot in said cylinder parallel to the axis of said cylinder and an extension from said operating rod slidably engaging said slot; said extension from said operating rod moving up and down with respect to said cylinder as said operating rod is translated circularly around the axis of its own housing; said operating rod, owing to the fact that it is also moved longitudinally, by reason of the engagement of the cam and the cam follower head, oscillating said cylinder over a substantial angle during each translated revolution of the operating rod about said axis.

4. The dental device of claims 1 or 3, wherein said cylinder is connected to and carries a prophylactic cup and said cup oscillates owing to the oscillation of said cylinder.

5. The dental device of claim 3, wherein the cylinder and the device carried thereby is oscillated over an arc of 50° to 120° in response to the reciprocal movement of the operating rod.

6. The dental device of claim 5, wherein the rod carrying block is rotated at a speed of up to 3,500 rpm and above.

7. The dental device of claim 5, wherein the operating members rotate at a speed ranging up to 3,500 rpm and further up to 12,000 rpm.

* * * * *